United States Patent [19]

Kim

[11] Plant 4,054

[45] May 10, 1977

[54] *SCINDAPSUS AUREUS* MARBLE QUEEN HEEYOUNG KIM

[76] Inventor: Heeyoung Kim, 922 W. Lee Drive, Santa Maria, Calif. 93454

[21] Appl. No.: 693,788

[22] Filed: June 15, 1976

[51] Int. Cl.[2] ..... A01H 5/12

[52] U.S. Cl. ..... Plt./88

[58] Field of Search ..... Plt./88

*Primary Examiner*—Robert E. Bagwill

EXEMPLARY CLAIM

1. A novel variety of Scindapsus, which differs from its parent, Scindapsus Marble Queen, by having larger, more rounded, more intensely colored leaves, and thicker stems.

1 Drawing Figure

The present invention comprises a novel Scindapsus plant which is a large-leaved mutation of the variety, Scindapsus Marble Queen. The new variety is named S. Marble Queen Heeyoung Kim, and was originated by applying a 10% solution of colchicine to a new bud of the parent plant, three times weekly. The parent plant was being grown in a soil mix comprised of two parts of peat moss to one part of perlite, at a temperature of 70° F and 80% humidity. The mutation arising from said bud was propagated by cuttings placed in a mixture of 2 parts redwood shavings, 1 part peat moss, 1 part top soil, and mineral fertilizer. The new variety was propagated three successive times without reversion to the parent leaf size.

The new variety is readily distinguished from the parent variety by its larger leaves which are more rounded in shape, leaf colors of white and green which are more intense, and by its thicker stems. The following table enumerates the differences:

| | Leaf Area | Leaf Length | Leaf Width | Stem Thickness |
|---|---|---|---|---|
| New Variety | 152.5 cm² | 17.0 cm | 12.7 cm | 3/8" |
| Parent | 76.1 cm² | 12.2 cm | 8.5 cm | 3/16" |

The attached drawings illustrate the novel characteristics, with the new variety appearing in the left of each print.

I claim:

1. A novel variety of Scindapsus, which differs from its parent, Scindapsus Marble Queen, by having larger, more rounded, more intensely colored leaves, and thicker stems.

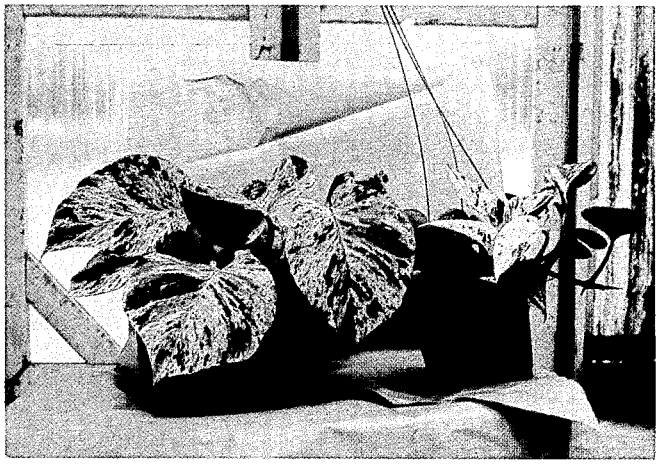
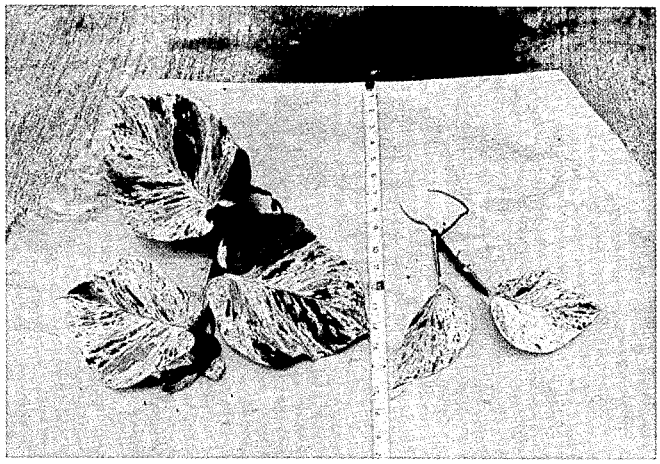

* * * * *